United States Patent
Tian

(10) Patent No.: US 11,730,692 B2
(45) Date of Patent: Aug. 22, 2023

(54) INSTANT HAND-PROTECTION ANTIBACTERIAL GEL, METHOD FOR PREPARING THE SAME AND USE OF THE SAME

(71) Applicant: NANJING LETOP BIOTECHNOLOGY CO., LTD., Jiangsu (CN)

(72) Inventor: Yue Tian, Jiangsu (CN)

(73) Assignee: Nanjing Letop Biotechnology Co., Ltd., Jiangsu (CN)

( * ) Notice: Subject to any disclaimer, the term of this patent is extended or adjusted under 35 U.S.C. 154(b) by 0 days.

(21) Appl. No.: 17/423,904

(22) PCT Filed: Nov. 4, 2020

(86) PCT No.: PCT/CN2020/126394
§ 371 (c)(1),
(2) Date: Jul. 19, 2021

(87) PCT Pub. No.: WO2022/067960
PCT Pub. Date: Apr. 7, 2022

(65) Prior Publication Data
US 2022/0142902 A1    May 12, 2022

(30) Foreign Application Priority Data
Sep. 30, 2020   (CN) .......................... 202011066052.0

(51) Int. Cl.
| | | |
|---|---|---|
| A61Q 17/00 | (2006.01) | |
| A61K 8/73 | (2006.01) | |
| A61K 8/04 | (2006.01) | |
| A61K 8/34 | (2006.01) | |
| A61K 8/49 | (2006.01) | |
| A61K 8/60 | (2006.01) | |

(52) U.S. Cl.
CPC .............. *A61K 8/735* (2013.01); *A61K 8/042* (2013.01); *A61K 8/34* (2013.01); *A61K 8/4926* (2013.01); *A61K 8/4946* (2013.01); *A61K 8/608* (2013.01); *A61K 8/731* (2013.01); *A61Q 17/005* (2013.01); *A61K 2800/48* (2013.01); *A61K 2800/70* (2013.01)

(58) Field of Classification Search
None
See application file for complete search history.

(56) References Cited

U.S. PATENT DOCUMENTS

| | | | |
|---|---|---|---|
| 6,096,324 A | 8/2000 | Mansouri | |
| 2010/0158993 A1* | 6/2010 | Spann-Wade | A61K 31/192 514/420 |
| 2020/0046631 A1* | 2/2020 | Jin | A61K 8/9789 |

FOREIGN PATENT DOCUMENTS

| | | |
|---|---|---|
| CN | 101658469 | 3/2010 |
| CN | 104840410 | 8/2015 |
| CN | 106214573 | 12/2016 |
| CN | 107550818 | 1/2018 |
| CN | 107648085 | 2/2018 |
| CN | 110433113 | 11/2019 |
| CN | 111419741 | 7/2020 |

OTHER PUBLICATIONS

Ya-Qing Li, "Development of a type of wash-free disinfection alcohol gel," Journal of Liaoning Normal Colleges (Natural Science Edition), vol. 22, No. 2, Jun. 2020, pp. 1-3.
"International Search Report (Form PCT/ISA/210) of PCT/CN2020/126394," dated Jun. 29, 2021, pp. 1-5.

* cited by examiner

*Primary Examiner* — Jyothsna A Venkat
(74) *Attorney, Agent, or Firm* — JCIP Global Inc.

(57) ABSTRACT

The invention discloses an instant hand-protection antibacterial gel, a method for preparing the same and use of the same, and belongs to the technical field of antibacterial disinfection. The instant hand-protection antibacterial gel of the present invention comprises: hydrolyzed sodium hyaluronate 0.01-0.5%, keratin care agent 0.01%-5%, thickener 0.1-0.5%, emollient 1-10%, pH regulator 0.1-0.5%, ethanol 56-75%, and the balance is water; and an average molecular weight of the hydrolyzed sodium hyaluronate is one or more of 500-20000 Daltons.

1 Claim, 2 Drawing Sheets

INSTANT HAND-PROTECTION ANTIBACTERIAL GEL, METHOD FOR PREPARING THE SAME AND USE OF THE SAME

CROSS-REFERENCE TO RELATED APPLICATION

This application is a 371 of international application of PCT application serial no. PCT/CN2020/126394, filed on Nov. 4, 2020, which claims the priority benefit of China application no. 202011066052.0, filed on Sep. 30, 2020. The entirety of each of the above mentioned patent applications is hereby incorporated by reference herein and made a part of this specification.

BACKGROUND

Technical Field

The invention relates to an instant hand-protection antibacterial gel and preparation method thereof, and belongs to the technical field of antibacterial disinfection.

Description of Related Art

With the progress of society, the continuous improvement of living standards and the change of consumer concepts, the frequency and requirements of using hand washing and disinfection supplies by people are also increasing, usage mode is slowly changing from soap to hand sanitizer. With the popularization of hand sanitizer, people's requirements for hand sanitizer are no longer single, which gradually expand from washing to disinfection, sterilization, instant and other functions. The word of instant in the present invention means no-clean. Therefore, hand sanitizers with various functions are constantly coming out, and instant disinfectants are gradually entering the field of vision. Compared with general disinfectant, instant disinfectant can play a disinfection role without running water to rinse and the use is not restricted by region. It is especially suitable for people who work or travel outdoors, such as drivers, students and travelers, etc.

There are many varieties of disinfectants in the existing market, although the killing rate is more than 90% for common pathogens such as *Candida albicans, Staphylococcus aureus*, and *Escherichia coli*, there are some problems in the use of commonly instant disinfectants. For example, some disinfectants cause severe skin dryness, chapped and even peeling after use; some disinfectants use high-concentration alcohol as a solvent, which has a strong taste and severe irritation; some disinfectants are viscous, resulting in a poor quick-drying effect, and producing a sticky feeling. Chinese patent application CN106214573A discloses a method for preparing a medical instant hand-protection disinfectant, which adds hydrogen peroxide and medical alcohol as the main disinfectant, supplemented by a variety of Chinese medicine extracts as auxiliary disinfection. But the quick-drying effect is poor and the antibacterial component of cassonne is added. The European Union has made it clear that cassonne can only be used in non-resident washing products. Therefore, in fact, the disinfectant still needs to be rinsed with running water to meet the requirements, and the production cost is higher. Chinese patent application CN104840410A discloses a no hand-clean disinfectant, preparation and application thereof, which uses 3-5% triclocarban solution and alcohol as bactericidal and antibacterial ingredients. Although the disinfection effect is good, N,N-dimethylformamide and other organic solvents are added. While N,N-dimethylformamide is included in the list of 2A carcinogens, which with potential carcinogenic risks.

In summary, the existing instant disinfectants in the market mainly use alcohol solvents or chlorine-containing compounds such as triclosan as the main functional additives, and use higher alcohols such as ethanol, n-propanol or isopropanol as the main solvents. International studies have shown that alcohol disinfectants are not only safe, reliable and quick dry, but also have a broad-spectrum sterilization effect. The range of ethanol sterilization is that the concentration of ethanol is not less than 60%, and the best concentration of ethanol sterilization is 75%. If the concentration of ethanol is too high, it will have a strong unacceptable pungent odor; if the concentration is too low, the sterilization effect will be reduced. The use of chlorine-containing disinfectants can cause skin allergies and other problems, and the alcohol-based disinfectants can cause dry and chapped skin. Therefore, how to achieve a good sterilization effect while using a non-sticky disinfectant gel that can play a role in skin care and moisturizing is an urgent problem to be solved.

SUMMARY

The purpose of the present invention is to solve the technical deficiencies of the existing products in the market, such as stickiness, dry and chapped skin, etc., and to develop a no-clean hand-care antibacterial gel, which has a strong bactericidal effect. The germicidal rate can reach more than 99.9% for common pathogens such as *Staphylococcus aureus, Candida albicans* and *Escherichia coli*, and the sterilization lasts for a long time. After use, there is no sticky feeling and chapped phenomenon, and can achieve the effect of moisturizing, nourishing and caring for hands.

In order to solve the above technical problems, the present invention firstly provides a no-clean hand-care antibacterial gel, which comprises the following raw materials in mass proportion: hydrolyzed sodium hyaluronate 0.01-0.5%, keratin care agent 0.01%-5%, thickener 0.1-0.5%, emollient 1-10%, pH regulator 0.1-0.5%, ethanol 56-75%, and a balance is water. An average molecular weight of the hydrolyzed sodium hyaluronate is one or more of 500-20000 Dalton.

In an embodiment of the present invention, the raw material may optionally comprise a macromolecular sodium hyaluronate with a mass proportion of 0-0.5%; an average molecular weight of the macromolecular sodium hyaluronate is one or more of $1 \times 10^6$-$2.2 \times 10^6$ Dalton.

In one embodiment of the present invention, an average molecular weight of the hydrolyzed sodium hyaluronate is preferably selected from one or more of 1000 Da, 5000 Da and 20000 Da.

In one embodiment of the present invention, the keratin care agent comprises one or more of allantoin, trehalose, oat β-glucan and nicotinamide.

In one embodiment of the present invention, the keratin care agent is preferably allantoin or trehalose.

In one embodiment of the present invention, the thickener comprises one or more of carbomer, hydroxyethyl cellulose, hydroxypropyl cellulose, and hydroxypropyl methyl cellulose.

In one embodiment of the present invention, the thickener is preferably carbomer or hydroxyethyl cellulose.

In one embodiment of the present invention, the emollient comprises one or more of glycerin, butylene glycol, vitamin E, vitamin E acetate, and isopropyl myristate.

In one embodiment of the present invention, the emollient is a combination of glycerin and butylene glycol with the mass proportion of 1:100-100:1.

In one embodiment of the present invention, the mass proportion of the glycerin and butylene glycol is preferably 1:1.

In one embodiment of the present invention, the pH regulator is triethanolamine or sodium hydroxide.

The second purpose of the present invention is to provide a method for preparing the above-mentioned instant hand-protection antibacterial gel, which comprises the following steps:

(1) weighing each component according to proportion, adding 30-90% of a required amount of water to a reactor, adding the thickener to the reactor, stirring the mixture slowly, adding hydrolyzed sodium hyaluronate, stirring at 100-200 r/min and 25-50° C. for 0.5-2 hours, disposing the mixture in still stand for fully swelling to obtain a phase A liquid;

(2) adding, in another reactor, ethanol in 20-70% of a total mass of the instant hand-protection antibacterial gel, adding the keratin care agent to mix and dissolve, physically stirring the mixture at 100-200 r/min until the solution is clear to obtain a phase B liquid, and sealing and preserving the phase B liquid;

(3) adding the phase B liquid slowly to the phase A liquid while stirring, stirring the mixture uniformly at a rotating speed of 100-200 r/min, then adding the emollient, balance water and balance ethanol in turns, adjusting a pH to 6.0-8.0 with the pH regulator to obtain the instant hand-protection antibacterial gel.

In one embodiment of the present invention, when the instant hand-protection antibacterial gel contains macromolecular sodium hyaluronate, it is added to the reactor together with the hydrolyzed sodium hyaluronate described in step (1).

In one embodiment of the present invention, the time for stewing and fully swelling is 3-4 hours in step (1).

The third purpose of the present invention is to provide the application of the above-mentioned no-clean hand-care antibacterial gel in the technical field of antibacterial disinfection.

In one embodiment of the present invention, the no-clean hand-care antibacterial gel has the functions of disinfection, moisturizing and nursing at the same time. Among them, after 10 minutes disinfecting for the common pathogenic bacteria such as *Escherichia coli, Staphylococcus aureus*, and *Candida albicans*, the bactericidal rate can reach more than 99.9%, while achieving multi-level moisturizing and nursing effect.

The beneficial effects of the present invention are as follows:

(1) The instant hand-protection antibacterial gel integrates disinfection, moisturizing, hand-care and no-clean. Its effective sterilization component is ethanol, which has high sterilization efficiency, fast speed, non-toxicity and no residue. One or two kinds of macromolecular sodium hyaluronate and One two or three kinds of hydrolyzed sodium hyaluronate is added, which can achieve the combined efficacy of disinfection and moisturizing care, and make the antibacterial gel convenient to use and comfortable to touch.

(2) Macromolecular sodium hyaluronate was added optionally to the product of the invention. Macromolecular sodium hyaluronate is a large polysaccharide compound that can carry more than 500 times of water, which can improve the nutrition metabolism of the skin, thus make the skin smooth, unwrinkle, and increase the skin elastic. Macromolecular sodium hyaluronate not only has moisturizing effect, but also has a good effect of promoting transdermal absorption.

(3) A variety of hydrolyzed sodium hyaluronate was added to the product of the invention. Hydrolyzed sodium hyaluronate is a neutral mucopolysaccharide prepared by fermentative hydrolysis of macromolecular hyaluronic acid. The smaller the molecular weight of hydrolyzed sodium hyaluronate is, the better the effect. The molecular weight of hydrolyzed sodium hyaluronate is less than 20,000 Daltons, the transdermal absorption effect is increased and deep moisturizing achieved. The hydrolyzed sodium hyaluronate combined with macromolecular weight hyaluronic acid can achieve multi-level moisturizing nursing effect.

(4) Strict experimental conditions have proved that the product of the invention has a disinfection effect on common pathogens such as *Staphylococcus aureus, Candida albicans, Escherichia coli, Pseudomonas aeruginosa*, etc. for 10 minutes, the sterilization rate is more than 85%, up to 99.9%, and the moisturizing effect is good, up to 2 times of the original.

(5) When using butanediol and glycerin as emollients at the same time, although the ethanol content is only 68%, the antibacterial efficiency of the product can reach more than 99%, which is basically the same as that of the product with 75% ethanol. The technical scheme of the present invention can obviously save the content of ethanol, and can also reduce the type and amount of hydrolyzed sodium hyaluronate, thereby saving production costs and having a wide range of market application scenarios.

DESCRIPTION OF THE EMBODIMENTS

Figure 1:
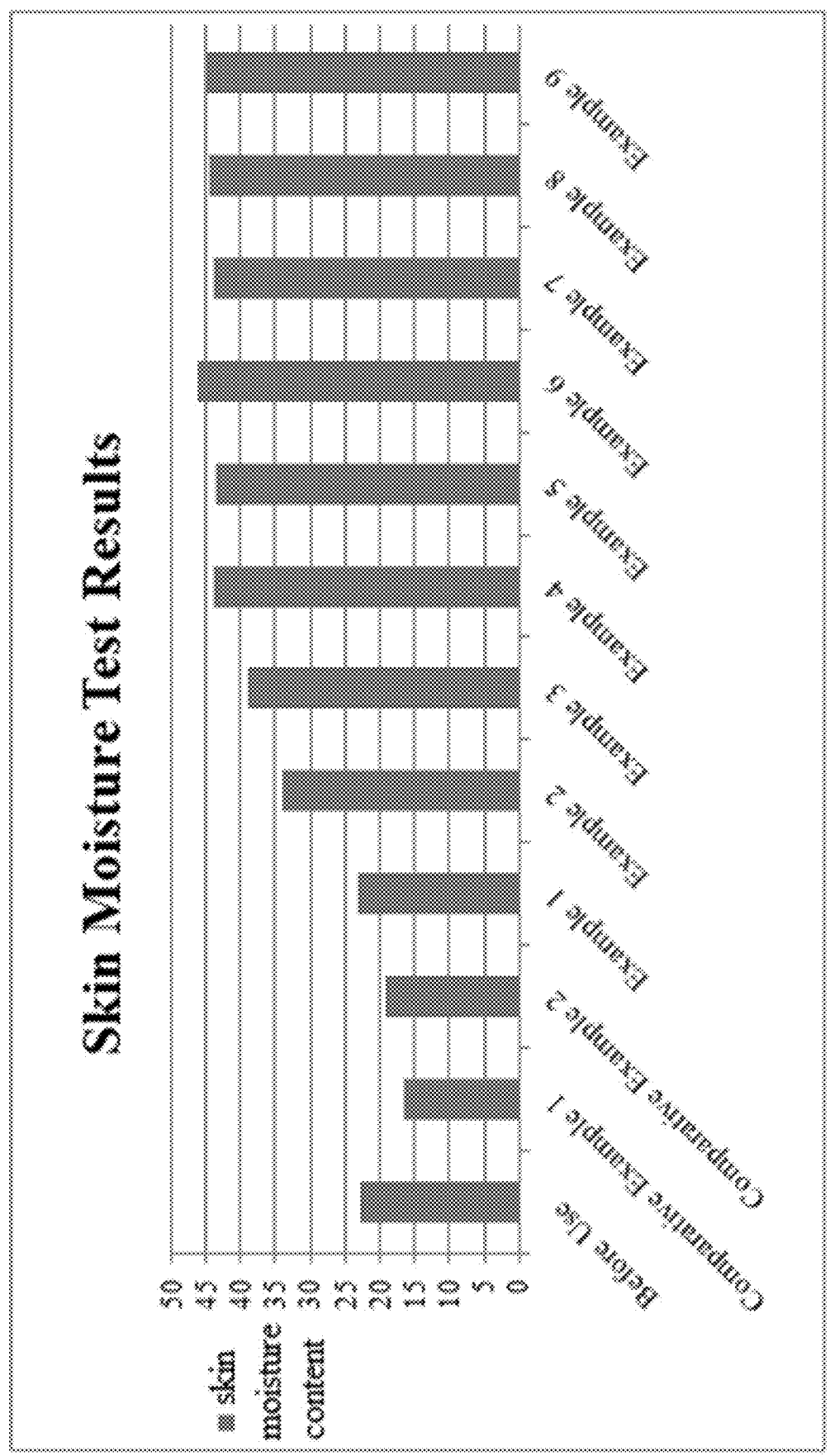
FIG. 1 shows the skin moisture test results of the instant hand-protection antibacterial gel prepared in Examples 1-7 and Comparative Examples 1-2.

In order to facilitate those skilled in the art to understand the content of the present invention, the technical solutions of the present invention will be further described below in conjunction with specific embodiments, but the following content should not limit the scope of the invention claimed by the appended claims in any way.

In Examples 1-3, the other ingredients and contents in formula were the same, and the effects of different average molecular weight and contents of macromolecular sodium hyaluronate, hydrolyzed sodium hyaluronate, and ethanol content on the sterilization efficacy and moisturizing efficacy of the formula were investigated.

Example 1

A kind of instant hand-protection antibacterial gel, including the following raw materials in mass proportion: macromolecular sodium hyaluronate ($1.0\times10^6$ Daltons) 0.01%, hydrolyzed sodium hyaluronate (1000 Daltons) 0.01%, hydrolyzed sodium hyaluronate (5000 Daltons) 0.02%, allantoin 0.1%, carbomer 0.2%, vitamin E acetate 8%, triethanolamine pH regulator 0.5%, ethanol 60%, and a balance is water.

The method for preparing the no-clean hand-care antibacterial gel can be implemented as follows:

(1) Each component in proportion was weighted, 90% of the required amount of water was added to the reactor, then the thickener was added to the reactor, the mixture was stirred slowly, macromolecular sodium hyaluronate and hydrolyzed sodium hyaluronate were added, stirred at 100-200 r/min at 50° C. for 2 hours, and the mixture was stewed and fully swelled for 3 hours to obtain phase A liquid;

(2) In another reactor, 50% ethanol of the total mass of the no-clean hand-care antibacterial gel was added, then the keratin care agent was mixed and dissolved, the mixture was stirred mechanically at 100-200 r/min until the solution was clear to obtain phase B liquid, which then sealed and preserved;

(3) Phase B liquid was added slowly to phase A liquid while stirring. The mixture was stirred uniformly at a rotating speed of 100-200 r/min. Then the emollient, remaining water and remaining ethanol were added in turns, the pH was adjusted to 7.0 with pH regulator to get the no-clean hand-care antibacterial gel.

Example 2

A kind of instant hand-protection antibacterial gel, including the following raw materials in mass proportion: macromolecular sodium hyaluronate ($1.6\times10^6$ Daltons) 0.01%, hydrolyzed sodium hyaluronate (1000 Daltons) 0.05%, hydrolyzed sodium hyaluronate (5000 Daltons) 0.05% and hydrolyzed sodium hyaluronate (20000 Daltons) 0.2%, allantoin 0.1%, carbomer 0.2%, vitamin E acetate 8%, triethanolamine pH regulator 0.5%, ethanol 65%, and a balance is water.

The method for preparing the no-clean hand-care antibacterial gel can be implemented as follows:

(1) Each component in proportion was weighted, 90% of the required amount of water was added to the reactor, then the thickener was added to the reactor, the mixture was stirred slowly, macromolecular sodium hyaluronate and hydrolyzed sodium hyaluronate were added, stirred at 100-200 r/min at 50° C. for 2 hours, and the mixture was stewed and fully swelled for 3 hours to obtain phase A liquid;

(2) In another reactor, 50% ethanol of the total mass of the no-clean hand-care antibacterial gel was added, then the keratin care agent was mixed and dissolved, the mixture was stirred mechanically at 100-200 r/min until the solution was clear to obtain phase B liquid, which then sealed and preserved;

(3) Phase B liquid was added slowly to phase A liquid while stirring. The mixture was stirred uniformly at a rotating speed of 100-200 r/min. Then the emollient, remaining water and remaining ethanol were added in turns, the pH was adjusted to 7.0 with pH regulator to get the no-clean hand-care antibacterial gel.

Example 3

A kind of instant hand-protection antibacterial gel, including the following raw materials in mass proportion: macromolecular sodium hyaluronate ($1.6\times10^6$ Daltons) 0.1%, hydrolyzed sodium hyaluronate (1000 Daltons) 0.05%, hydrolyzed sodium hyaluronate (5000 Daltons) 0.16%, hydrolyzed sodium hyaluronate (20000 Daltons) 0.1%, allantoin 0.1%, carbomer 0.2%, vitamin E acetate 8%, triethanolamine pH regulator 0.5%, ethanol 70%, and a balance is water.

The method for preparing the no-clean hand-care antibacterial gel can be implemented as follows:

(1) Each component in proportion was weighted, 90% of the required amount of water was added to the reactor, then the thickener was added to the reactor, the mixture was stirred slowly, macromolecular sodium hyaluronate and hydrolyzed sodium hyaluronate were added, stirred at 100-200 r/min at 50° C. for 2 hours, and the mixture was stewed and fully swelled for 3 hours to obtain phase A liquid;

(2) In another reactor, 50% ethanol of the total mass of the no-clean hand-care antibacterial gel was added, then the keratin care agent was mixed and dissolved, the mixture was stirred mechanically at 100-200 r/min until the solution was clear to obtain phase B liquid, which then sealed and preserved;

(3) Phase B liquid was added slowly to phase A liquid while stirring. The mixture was stirred uniformly at a rotating speed of 100-200 r/min. Then the emollient, remaining water and remaining ethanol were added in turns, the pH was adjusted to 7.0 with a pH regulator to get the no-clean hand-care antibacterial gel.

Examples 4-6 investigated the influence of different types of emollients in the formula on the antibacterial efficacy of the formula.

Example 4 (without Adding Macromolecular Sodium Hyaluronate and 20,000 Da Hydrolyzed Sodium Hyaluronate)

A kind of instant hand-protection antibacterial gel, including the following raw materials in mass proportion: hydrolyzed sodium hyaluronate (1000 Daltons) 0.01%, hydrolyzed sodium hyaluronate (5000 Daltons) 0.01%, allantoin 0.01%, carbomer 0.3%, glycerol 8%, triethanolamine 0.3%, ethanol 68%, and a balance is water.

The method for preparing the no-clean hand-care antibacterial gel can be implemented as follows:

(1) Each component in proportion was weighted, 90% of the required amount of water was added to the reactor, the thickener was added to the reactor, the mixture was stirred slowly, hydrolyzed sodium hyaluronate was added, stirred at 100-200 r/min at 50° C. for 2 hours, and the mixture was stewed and fully swelled for 3 hours to obtain phase A liquid;

(2) In another reactor, 50% ethanol of the total mass of the no-clean hand-care antibacterial gel was added, then the keratin care agent was mixed and dissolved, the mixture was stirred mechanically at 100-200 r/min until the solution was clear to obtain phase B liquid, which then sealed and preserved;

(3) Phase B liquid was added slowly to phase A liquid while stirring. The mixture was stirred uniformly at a rotating speed of 100-200 r/min. Then the emollient, remaining water and remaining ethanol were added in turns, the pH was adjusted to 7.0 with pH regulator to get the no-clean hand-care antibacterial gel.

Example 5 (without Adding Macromolecular Sodium Hyaluronate and 20,000 Da Hydrolyzed Sodium Hyaluronate)

A kind of instant hand-protection antibacterial gel, including the following raw materials in mass proportion: hydrolyzed sodium hyaluronate (1000 Daltons) 0.01%, hydrolyzed sodium hyaluronate (5000 Daltons) 0.01%, allantoin 0.01%, carbomer 0.3%, butanediol 8%, triethanolamine 0.3%, ethanol 68%, and a balance is water.

The method for preparing the instant hand-care antibacterial gel can be implemented as follows:

(1) Each component in proportion was weighed, 90% of the required amount of water was added to the reactor, the thickener was added to the reactor, the mixture was stirred slowly, hydrolyzed sodium hyaluronate was added, stirred at 100-200 r/min at 50° C. for 2 hours, and the mixture was stewed and fully swelled for 3 hours to obtain phase A liquid;

(2) In another reactor, 50% ethanol of the total mass of the no-clean hand-care antibacterial gel was added, then the keratin care agent was mixed and dissolved, the mixture was stirred mechanically at 100-200 r/min until the solution was clear to obtain phase B liquid, which then sealed and preserved;

(3) Phase B liquid was added slowly to phase A liquid while stirring. The mixture was stirred uniformly at a rotating speed of 100-200 r/min. Then the emollient, remaining water and remaining ethanol were added in turns, the pH was adjusted to 7.0 with pH regulator to get the no-clean hand-care antibacterial gel.

Example 6 (without Adding Macromolecular Sodium Hyaluronate and 20,000 Da Hydrolyzed Sodium Hyaluronate)

A kind of instant hand-protection antibacterial gel, including the following raw materials in mass proportion: hydrolyzed sodium hyaluronate (1000 Daltons) 0.01%, hydrolyzed sodium hyaluronate (5000 Daltons) 0.01%, allantoin 0.01%, carbomer 0.3%, glycerol 4%, butanediol 4%, triethanolamine 0.3%, ethanol 68%, and a balance is water.

The method for preparing the no-clean hand-care antibacterial gel can be implemented as follows:

(1) Each component in proportion was weighted, 90% of the required amount of water was added to the reactor, the thickener was added to the reactor, the mixture was stirred slowly, hydrolyzed sodium hyaluronate was added, stirred at 100-200 r/min at 50° C. for 2 hours, and the mixture was stewed and fully swelled for 3 hours to obtain phase A liquid;

(2) In another reactor, 50% ethanol of the total mass of the no-clean hand-care antibacterial gel was added, the keratin care agent to mixed and dissolved, the mixture was stirred mechanically at 100-200 r/min until the solution was clear to obtain phase B liquid, which then sealed and preserved;

(3) Phase B liquid was added slowly to phase A liquid while stirring, the mixture was stirred uniformly at a rotating speed of 100-200 r/min. Then the emollient, remaining water and remaining ethanol were added in turns, the pH was adjusted to 7.0 with pH regulator to get the no-clean hand-care antibacterial gel.

Examples 7-9 investigated the influence of the types and contents of various ingredients in the formula on the antibacterial efficacy and moisturizing efficacy of the formula.

Example 7

A kind of instant hand-protection antibacterial gel, including the following raw materials in mass proportion: macromolecular sodium hyaluronate ($1.0 \times 10^6$ Daltons) 0.5%, hydrolyzed sodium hyaluronate (1000 Daltons) 0.15%, hydrolyzed sodium hyaluronate (5000 Daltons) 0.06%, hydrolyzed sodium hyaluronate (20000 Daltons) 0.22%, trehalose 0.2%, hydroxyethyl cellulose 0.5%, vitamin E 8%, sodium hydroxide pH regulator 0.5%, ethanol 75%, and a balance is water.

The method for preparing the no-clean hand-care antibacterial gel can be implemented as follows:

(1) Each component in proportion was weighted, 90% of the required amount of water was added to the reactor, the thickener was added to the reactor, the mixture was stirred slowly, macromolecular sodium hyaluronate and hydrolyzed sodium hyaluronate were added, stirred at 100-200 r/min at 50° C. for 2 hours, and the mixture was stewed and fully swelled for 3 hours to obtain phase A liquid;

(2) In another reactor, 50% ethanol of the total mass of the no-clean hand-care antibacterial gel was added, the keratin care agent was mixed and dissolved, the mixture was stirred mechanically at 100-200 r/min until the solution was clear to obtain phase B liquid, which then sealed and preserved;

(3) Phase B liquid was added slowly to phase A liquid while stirring, the mixture was stirred uniformly at a rotating speed of 100-200 r/min, then the emollient, remaining water and remaining ethanol were added in turns, the pH was adjusted to 7.0 with pH regulator to get the no-clean hand-care antibacterial gel.

Example 8

A kind of instant hand-protection antibacterial gel, including the following raw materials in mass proportion: macromolecular sodium hyaluronate ($2 \times 10^6$ Daltons) 0.25%, hydrolyzed sodium hyaluronate (1000 Daltons) 0.18%, hydrolyzed sodium hyaluronate (5000 Daltons) 0.1%, hydrolyzed sodium hyaluronate (20000 Daltons) 0.22%, oat β-glucan 0.2%, hydroxypropyl cellulose 0.1%, isopropyl myristate 8%, sodium hydroxide pH regulator 0.5%, ethanol 75%, and a balance is water.

The method for preparing the no-clean hand-care antibacterial gel can be implemented as follows:

(1) Each component in proportion was weighed, 90% of the required amount of water was added to the reactor, then the thickener was added to the reactor, the mixture was stirred slowly, macromolecular sodium hyaluronate and hydrolyzed sodium hyaluronate were added, stirred at 100-200 r/min at 50° C. for 2 hours, and the mixture was stewed and fully swelled for 3 hours to obtain phase A liquid;

(2) In another reactor, 50% ethanol of the total mass of the no-clean hand-care antibacterial gel was added, then added the keratin care agent was mixed and dissolved, the mixture was stirred mechanically at 100-200 r/min until the solution was clear to obtain phase B liquid, which then sealed and preserved;

(3) Phase B liquid was added slowly to phase A liquid while stirring, the mixture was stirred uniformly at a rotating speed of 100-200 r/min, then the emollient, remaining water and remaining ethanol were added in turns, the pH was adjusted to 7.0 with pH regulator to get the no-clean hand-care antibacterial gel.

Example 9

A kind of instant hand-protection antibacterial gel, including the following raw materials in mass proportion: macromolecular sodium hyaluronate ($2.2 \times 10^6$ Daltons) 0.23%, hydrolyzed sodium hyaluronate (1000 Daltons) 0.2%, hydrolyzed sodium hyaluronate (5000 Daltons) 0.2%, hydrolyzed sodium hyaluronate (20000 Daltons) 0.1%, nicotinamide 0.2%, hydroxypropyl methylcellulose 0.1%, vitamin E 8%, hydroxide Sodium pH regulator 0.5%, ethanol 75%, and a balance is water.

The method for preparing the no-clean hand-care antibacterial gel can be implemented as follows:

(1) Each component in proportion was weighted, 90% of the required amount of water was added to the reactor, then the thickener was added to the reactor, the mixture was stirred slowly, macromolecular sodium hyaluronate and hydrolyzed sodium hyaluronate were added, stirred at 100-200 r/min at 50° C. for 2 hours, and the mixture was stewed and fully swelled for 3 hours to obtain phase A liquid;

(2) In another reactor, 50% ethanol of the total mass of the no-clean hand-care antibacterial gel was added, the keratin care agent was mixed and dissolved, the mixture was stirred mechanically at 100-200 r/min until the solution was clear to obtain phase B liquid, which then sealed and preserved;

(3) Phase B liquid was added slowly to phase A liquid while stirring. The mixture was stirred uniformly at a rotating speed of 100-200 r/min, then the emollient, remaining water and remaining ethanol were added in turns, the pH was adjusted to 7.0 with pH regulator to get the no-clean hand-care antibacterial gel.

Comparative Example 1

Comparative Example 1 used a formula without macromolecular sodium hyaluronate and hydrolyzed sodium hyaluronate as a comparison, and the rest were the same as in Example 1.

A kind of instant hand-protection antibacterial gel, including the following raw materials in mass proportion: allantoin 0.1%, carbomer 0.2%, vitamin E acetate 8%, triethanolamine pH regulator 0.5%, ethanol 65%, and a balance is water.

The method for preparing the no-clean hand-care antibacterial gel can be implemented as follows:

(1) Each component in proportion was weighted, 90% of the required amount of water was added to the reactor, then the thickener was added to the reactor, the mixture was stirred slowly, then stirred at 100-200 r/min at 50° C. for 2 h, and stewed and fully swelled for 3 hours to obtain A phase liquid;

(2) In another reactor, 50% ethanol of the total mass of the no-clean hand-care antibacterial gel was added, the keratin care agent was mixed and dissolved, the mixture was stirred mechanically at 100-200 r/min until the solution was clear to obtain phase B liquid, which then sealed and preserved;

(3) Phase B liquid was added slowly to phase A liquid while stirring. The mixture was stirred uniformly at a rotating speed of 100-200 r/min. Then the emollient, remaining water and remaining ethanol were added in turns, the pH was adjusted to 7.0 with pH regulator to get the no-clean hand-care antibacterial gel.

Comparative Example 2

Comparative Example 2 used a formula without hydrolyzed sodium hyaluronate as a comparison, and the rest were the same as Example 1.

A kind of instant hand-protection antibacterial gel, including the following raw materials in mass proportion: macromolecular sodium hyaluronate 0.01% ($1.0 \times 10^6$ Daltons), allantoin 0.1%, carbomer 0.2%, vitamins E acetate 8%, triethanolamine pH regulator 0.5%, ethanol 65%, and a balance is water.

The method for preparing the no-clean hand-care antibacterial gel can be implemented as follows:

(1) Each component in proportion was weighted, 90% of the required amount of water was added to the reactor, then the thickener was added to the reactor, the mixture was stirred slowly, macromolecular sodium hyaluronate was added, stirred at 100-200 r/min at 50° C. for 2 h, and the mixture was stewed and fully swelled for 3 hours to obtain phase A liquid;

(2) In another reactor, 50% ethanol of the total mass of the no-clean hand-care antibacterial gel was added, the keratin care agent was mixed and dissolved, the mixture was stirred mechanically at 100-200 r/min until the solution was clear to obtain phase B liquid, which then sealed and preserved;

(3) Phase B liquid was added slowly to phase A liquid while stirring. The mixture was stirred uniformly at a rotating speed of 100-200 r/min. The emollient, remaining water and remaining ethanol were added in turns, the pH was adjusted to 7.0 with pH regulator to get the no-clean hand-care antibacterial gel.

Comparative Example 3

Comparative Example 3 used a different preparation process as a comparison, and the rest were the same as Example 1

The raw materials are: macromolecular sodium hyaluronate ($1.0 \times 10^6$ Daltons) 0.01%, hydrolyzed sodium hyaluronate (1000 Daltons) 0.01%, hydrolyzed sodium hyaluronate (5000 Daltons) 0.02%, allantoin 0.1%, carbomer 0.2%, vitamin E acetate 8%, triethanolamine pH regulator 0.5%, ethanol 65%, and a balance is water.

The method for preparing the no-clean hand-care antibacterial gel can be implemented as follows:

(1) Each component in proportion was weighted, 90% of the required amount of water was added to the reactor, then the thickener was added to the reactor, the mixture was stirred slowly, then stirred at 100-200 r/min at 50° C. for 2 h, and stewed and fully swelled for 3 hours to obtain A phase liquid;

(2) In another reactor, 50% ethanol of the total mass of the no-clean hand-care antibacterial gel was added, the keratin care agent was mixed and dissolved, the mixture was stirred mechanically at 100-200 r/min until the solution was clear to obtain phase B liquid, which then sealed and preserved;

(3) Phase B liquid was added slowly to phase A liquid while stirring to obtain a mixed phase. Macromolecular sodium hyaluronate and hydrolyzed sodium hyaluronate were added to the above mixed phase, the mixture was stirred uniformly at a rotating speed of 100-200 r/min, the emollient, remaining water and remaining ethanol were added in turns, the pH was adjusted to 7.0 with pH regulator to obtain a turbid no-clean hand-care antibacterial gel with solid insoluble matter.

The instant hand-protection antibacterial gel of Examples 1-9 and Comparative Example 1 and 2 of the present invention were used respectively to conduct antibacterial performance experiments and skin moisturizing effect experiments.

(1) Antibacterial Performance Experiments

The instant hand-protection antibacterial gel of Examples 1-9 and Comparative Examples 1-2 of the present invention were used respectively, and *Staphylococcus aureus*, *Candida albicans*, and *Escherichia coli* were selected as test strains for antibacterial performance experiments. This process was carried out in accordance with the method steps of the "Disinfection Technical Specification" (2002 Edition), and will not be repeated here.

The experimental results were shown in Table 1 below. The bactericidal effect in the table was the sterilization rate after 10 minutes of action.

TABLE 1

Comparative data of antibacterial performance experiments

| # | Content of Ethanol | Sterilization Rate of *Staphylococcus aureus* | Sterilization Rate of *Candida albicans* | Sterilization Rate of *Escherichia coli* |
|---|---|---|---|---|
| Example 1 | 60% | 86.90% | 87.61% | 88.86% |
| Example 2 | 65% | 91.20% | 91.45% | 92.45% |
| Example 3 | 70% | 99.45% | 99.85% | 99.88% |
| Example 4 | 68% | 94.95% | 94.56% | 95.88% |
| Example 5 | 68% | 96.22% | 96.62% | 98.74% |
| Example 6 | 68% | 99.95% | 99.91% | 99.93% |
| Example 7 | 75% | 99.96% | 99.98% | 99.95% |
| Example 8 | 75% | 99.95% | 99.96% | 99.98% |
| Example 9 | 75% | 99.96% | 99.98% | 99.98% |
| Comparative Example 1 | 65% | 87.80% | 87.65% | 89.13% |
| Comparative Example 2 | 65% | 86.95% | 88.12% | 88.15% |

The results showed that: the bactericidal effect of the instant hand-protection-antibacterial gel of the present invention was more than 85% on common bacteria, and the sterilization rate increased with the increase of the content of ethanol in the instant hand-protection antibacterial gel from Examples 1-3. Combining Comparative Example 1 and Comparative Example 2, it can be seen that the formulations containing the macromolecular sodium hyaluronate and hydrolyzed sodium hyaluronate in Examples 1-3 had no effect on the sterilization effect of bacteria, and the ethanol content played a major role in the killing of bacteria. It can be obtained from Examples 7-9 that when the content of ethanol in the formula reached 75%, the sterilization rate reached more than 99.9%. It can be obtained from Examples 4-6 that when butanediol was combined with glycerol, although the content of ethanol was only 68%, the antibacterial efficiency of the final product could reach more than 99%, which was comparable to that of the product with 75% content of ethanol. It indicated that the combination of butanediol, glycerin and ethanol made the product have a stronger antibacterial effect, and this proportioning method could greatly reduce the amount of ethanol.

Skin Moisturizing Effect Experiments

The instant hand-protection antibacterial gel of Examples 1-9 and Comparative Examples 1-2 of the present invention were respectively used, and 20 persons were selected as the experimental group for each Example or Comparative Example.

Drawn a coin-sized prototype mark on the inside of the subject's arm, and applied an equal amount of this product to the test site. The skin moisture tester was used to detect and record the skin moisture content to verify the moisturizing effect of the product after 30 minutes of application. The test results were shown in Table 2 as follows.

TABLE 2

Comparative data of skin moisture content

| Subject Number | Before Use | Comparative Example 1 | Comparative Example 2 | Example 1 | Example 2 | Example 3 | Example 4 |
|---|---|---|---|---|---|---|---|
| 1 | 28.1 | 20.1 | 20.6 | 21.2 | 35.6 | 40.3 | 48.3 |
| 2 | 21.3 | 15.7 | 19.5 | 20.2 | 26.3 | 33.5 | 44.3 |
| 3 | 24.8 | 16.8 | 17.8 | 18.3 | 30.2 | 33.2 | 45.6 |
| 4 | 20.9 | 18.4 | 21.3 | 22.3 | 32.3 | 34.3 | 40.2 |
| 5 | 27.6 | 19.5 | 20.0 | 20.3 | 33.5 | 35.8 | 42.1 |
| 6 | 22.5 | 13.5 | 19.3 | 21.5 | 30.8 | 32.6 | 39.8 |
| 7 | 14.8 | 10.8 | 14.5 | 13.6 | 30.4 | 33.8 | 38.8 |
| 8 | 21.6 | 18.6 | 19.8 | 21.3 | 40.8 | 42.6 | 44.5 |
| 9 | 22.8 | 19.5 | 20.3 | 28.3 | 36.8 | 38.3 | 42.8 |
| 10 | 25.8 | 22.6 | 23.0 | 25.3 | 35.9 | 39.5 | 43.9 |
| 11 | 17.9 | 12.3 | 16.0 | 20.5 | 30.5 | 35.6 | 42.1 |
| 12 | 26.4 | 15.5 | 18.8 | 25.6 | 36.6 | 39.6 | 42.1 |
| 13 | 26.3 | 15.8 | 19.8 | 23.5 | 35.6 | 40.2 | 45.7 |
| 14 | 26 | 14.3 | 19.8 | 24.5 | 28.2 | 39.6 | 44.5 |
| 15 | 28.4 | 20.5 | 21.5 | 25.6 | 35.6 | 42.2 | 46.7 |
| 16 | 15.1 | 13.5 | 15.5 | 20.5 | 26.5 | 43.5 | 45.3 |
| 17 | 20.6 | 20.9 | 21.5 | 30.5 | 43.5 | 46.5 | 46.5 |
| 18 | 16.4 | 12.6 | 16.5 | 25.6 | 35.6 | 42.3 | 43.5 |
| 19 | 30 | 15.3 | 23.5 | 28.3 | 36.9 | 45.2 | 45.8 |
| 20 | 17.9 | 11.5 | 15.5 | 25.8 | 33.5 | 38.5 | 40.5 |
| Average Value | 22.8 | 16.4 | 19.2 | 23.1 | 33.8 | 38.9 | 43.7 |

| Subject Number | Before Use | Example 5 | Example 6 | Example 7 | Example 8 | Example 9 |
|---|---|---|---|---|---|---|
| 1 | 28.1 | 42.5 | 48.4 | 46.3 | 44.3 | 46.2 |
| 2 | 21.3 | 42.3 | 44.3 | 42.6 | 44.2 | 43.5 |
| 3 | 24.8 | 43.2 | 45.8 | 42.5 | 45.2 | 46.2 |
| 4 | 20.9 | 40.2 | 44.9 | 40.3 | 43.5 | 43.2 |
| 5 | 27.6 | 40.2 | 45.9 | 41.2 | 46.2 | 45.2 |
| 6 | 22.5 | 41.1 | 43.8 | 40.6 | 43.1 | 42.3 |
| 7 | 14.8 | 42.2 | 45.9 | 40.8 | 46.5 | 44.2 |
| 8 | 21.6 | 43.5 | 48.5 | 46.2 | 44.5 | 46.2 |
| 9 | 22.8 | 42.6 | 42.5 | 40.3 | 43.3 | 42.1 |
| 10 | 25.8 | 43.6 | 43.8 | 44.2 | 44.5 | 44.3 |
| 11 | 17.9 | 45.8 | 45.9 | 45.6 | 44.2 | 46.2 |
| 12 | 26.4 | 41.1 | 48.3 | 48.2 | 44.5 | 46.3 |

TABLE 2-continued

Comparative data of skin moisture content

| 13 | 26.3 | 41.2 | 45.8 | 42.3 | 45.2 | 44.2 |
|---|---|---|---|---|---|---|
| 14 | 26 | 44.7 | 44.8 | 43.2 | 45.2 | 44.5 |
| 15 | 28.4 | 42.5 | 46.9 | 43.2 | 44.1 | 46.2 |
| 16 | 15.1 | 42.8 | 48.9 | 45.6 | 44.2 | 45.2 |
| 17 | 20.6 | 45.6 | 49.1 | 48.6 | 44.5 | 45.5 |
| 18 | 16.4 | 49.8 | 48.1 | 45.7 | 43.5 | 45.2 |
| 19 | 30 | 47.6 | 47.8 | 48.2 | 44.9 | 45.6 |
| 20 | 17.9 | 45.3 | 45.2 | 41.6 | 45.2 | 42.3 |
| Average Value | 22.8 | 43.4 | 46.2 | 43.9 | 44.5 | 44.7 |

After averaging the test values of Comparative Example 1-2 and Example 1-9, the graph was drawn as shown in FIG. 1.

The results showed that using Comparative Example 1 (macromolecular sodium hyaluronate and hydrolyzed sodium hyaluronate were not added in the formula) for 30 minutes, the skin moisture content was significantly reduced by 28%; using Comparative Example 2 (small molecule sodium hyaluronate was not added in the formula) for 30 minutes, the skin moisture content was slightly reduced by 16%; and when using the no-clean hand-care antibacterial gel of Examples 1-9 of the present invention for 30 minutes, it was found that the skin moisture moisturizing effect was much higher than Comparative Example 1 and Comparative Example 2, and it could be increased to 2.03 times as high as the original. The skin moisture moisturizing effect in Examples 1-9 was respectively increased to 1.01, 1.48, 1.70, 1.92, 1.90, 2.03, 1.93, 1.95, 1.96 times of those before use. The skin moisture content gradually increased as the content of hydrolyzed sodium hyaluronate increased according to Examples 1-3 and Examples 7-9. The more the content of hydrolyzed sodium hyaluronate with an average molecular weight of 1000 Daltons, the higher the skin moisture content. Comparing with the use of glycerin and/or butylene glycol as emollients in Examples 4-6 and the use of vitamin E acetate as emollients in Examples 1-3, the moisturizing effect of glycerin and/or butylene glycol was significantly higher than that of vitamin E acetate. Comparing with the use of glycerin and/or butylene glycol as emollients in Examples 4-6 and the use of vitamin E or isopropyl myristate in Examples 7-9, the effect in nourishing the skin was similar as a single component. When glycerin and butylene glycol acted synergistically, the moisturizing effect was significantly better than the single effect of the four components. However, because vitamin E and isopropyl myristate were oily care agents, the solubility of vitamin E and isopropyl myristate was not as good as that of glycerin and butylene glycol in the preparation process, resulting the appearance of the product not as good as in Examples 4-6. According to market research, the price of vitamin E and isopropyl myristate was higher than that of glycerin and butylene glycol. Therefore, it is the best combination when glycerin and butylene glycol are synergistically used. Among them, when glycerin and butylene glycol were used in combination in Example 6, the moisturizing effect was obviously better than that of using a single emollient.

Figure 2:
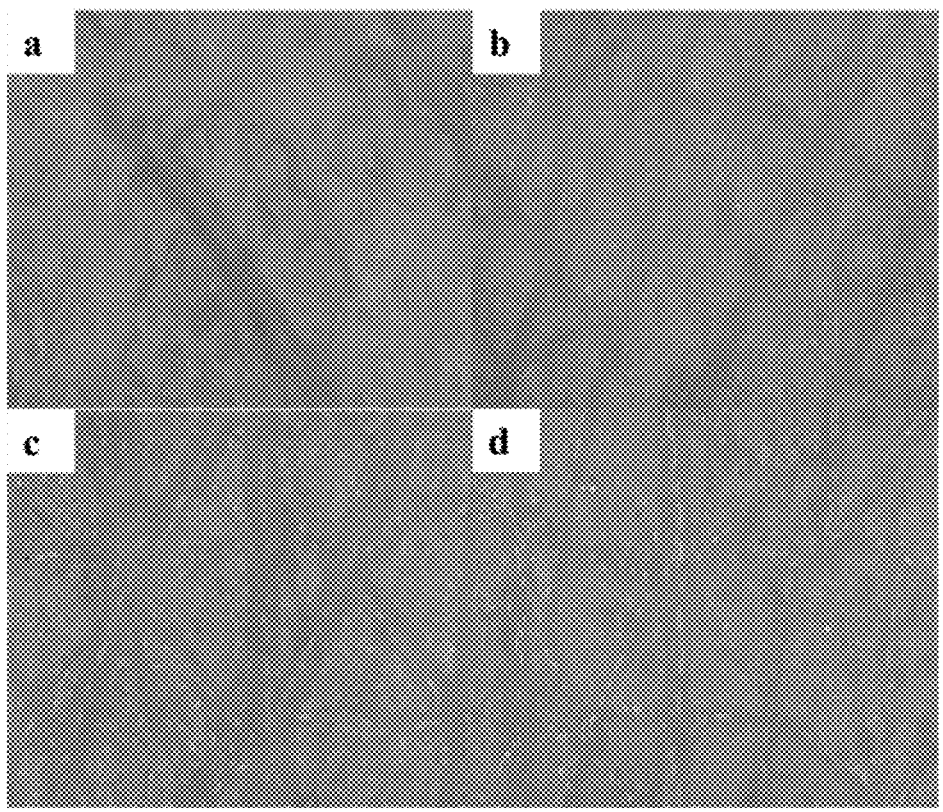
FIG. 2 shows the skin that has not been smeared and smeared with the instant hand-protection antibacterial gel prepared in Example 4 and Comparative Examples 1 and 2, wherein, a is normal skin, b is the skin after using the product of Comparative Example 1, c is the skin after using the product of Comparative Example 2, and d is the skin after using the product of Example 4.

After applying the product of Comparative Example 1-2 and Example 6 of the present invention for 30 minutes, the skin surface was observed through a microscope. The result was shown in FIG. 2, in which picture a was normal skin, picture b was the skin after using the product of Comparative Example 1, picture c was the skin after using the product of Comparative Example 2, and picture d was the skin after using the product of Example 4. It could be seen from FIG. 2 that a normal skin with obvious texture, deeper fine lines and dull; the skin was drier, the fine lines increased, and the skin appeared tight phenomenon after using Comparative Example 1; the skin was relatively moist, and the gloss began to appear after using Comparative Example 2; while the skin was very moist with high gloss, good water-locking effect, and no discomfort such as tightness on the skin after using the product of Example 6 of the present invention.

Sensory Evaluation and Results

The sensory test method was as follows: 15 subjects with numbered 1-15, age range from 24-50 years old and male to female ratio of 7:8, hands and forearms were cleaned respectively, the feeling of product use was evaluated. The specific method was as follows: washed your hands with water and wiped them before using the product, then 2 ml of the product was applied evenly to your hands and forearms for evaluation.

It mainly evaluated whether the appearance of the product was clear and transparent, whether it was too sticky, and whether it was comfortable to apply. The full score was 10 points, 10 points were the best, 1 point was the worst, and each item was scored 1-10 points, the details were seen in Table 3.

TABLE 3

Sensory evaluation and comparison of results

| | Appearance | | | | Sticky | | | |
|---|---|---|---|---|---|---|---|---|
| Number | Example 6 | Comparative Example 1 | Comparative Example 2 | Comparative Example 3 | Example 6 | Comparative Example 1 | Comparative Example 2 | Comparative Example 3 |
| 1 | 10 | 10 | 10 | 2 | 8 | 9 | 6 | 5 |
| 2 | 10 | 10 | 10 | 1 | 9 | 9 | 8 | 5 |
| 3 | 10 | 10 | 10 | 2 | 9 | 8 | 7 | 5 |
| 4 | 10 | 10 | 10 | 1 | 8 | 8 | 5 | 4 |
| 5 | 10 | 10 | 10 | 3 | 10 | 8 | 5 | 3 |
| 6 | 10 | 10 | 10 | 2 | 8 | 9 | 6 | 3 |
| 7 | 10 | 10 | 10 | 1 | 9 | 9 | 6 | 5 |

TABLE 3-continued

Sensory evaluation and comparison of results

| 8 | 10 | 10 | 10 | 1 | 9 | 9 | 8 | 6 |
|---|----|----|----|----|----|----|----|----|
| 9 | 10 | 10 | 10 | 1 | 8 | 8 | 6 | 3 |
| 10 | 10 | 10 | 10 | 3 | 8 | 8 | 9 | 3 |
| 11 | 10 | 10 | 10 | 4 | 6 | 9 | 9 | 2 |
| 12 | 10 | 10 | 10 | 2 | 8 | 9 | 5 | 5 |
| 13 | 10 | 10 | 10 | 3 | 8 | 10 | 5 | 5 |
| 14 | 10 | 10 | 10 | 3 | 9 | 10 | 6 | 6 |
| 15 | 10 | 10 | 10 | 3 | 8 | 10 | 6 | 4 |
| Average Score | 10 | 10 | 10 | 2 | 8 | 9 | 6 | 4 |

| | Smudge | | | |
|---|---|---|---|---|
| Number | Example 6 | Comparative Example 1 | Comparative Example 2 | Comparative Example 3 |
| 1 | 8 | 6 | 7 | 5 |
| 2 | 9 | 6 | 6 | 6 |
| 3 | 8 | 6 | 5 | 4 |
| 4 | 7 | 7 | 8 | 2 |
| 5 | 8 | 8 | 6 | 3 |
| 6 | 10 | 9 | 4 | 1 |
| 7 | 10 | 9 | 5 | 2 |
| 8 | 9 | 8 | 6 | 3 |
| 9 | 8 | 8 | 8 | 5 |
| 10 | 10 | 8 | 6 | 4 |
| 11 | 10 | 8 | 8 | 6 |
| 12 | 10 | 9 | 4 | 7 |
| 13 | 10 | 9 | 6 | 3 |
| 14 | 8 | 8 | 8 | 2 |
| 15 | 9 | 8 | 9 | 1 |
| Average Score | 9 | 7 | 6 | 4 |

From the comparison of the data in Table 3, it could be seen that the overall evaluation of Example 6 was higher than that of Comparative Examples 1-3. Among them, Example 6, Comparative Example 1, and Comparative Example 2 were clear and transparent in appearance, while Comparative Example 3 was a turbid gel with solid insoluble matter, so the score of Comparative Example 3 was low. Comparative Example 1 did not add any hyaluronic acid products, so its stickiness was not heavy. Because two kinds of low molecular weight hydrolyzed sodium hyaluronate were added in Example 6, so the evaluation of stickiness was high, while the products in Comparative Example 2 and Comparative Example 3 had strong stickiness and bad smear feeling due to the addition of high molecular weight sodium hyaluronate. Comprehensive evaluation, products of Example 6 had a clear and transparent appearance and a high evaluation of feeling in use.

Although the present invention has been disclosed as above in preferred embodiments, it is not intended to limit the present invention. Anyone familiar with this technology can make various changes and modifications without departing from the spirit and scope of the present invention. Therefore, the protection scope of the present invention should be defined by the claims.

What is claimed is:

1. An instant hand-protection antibacterial gel, consisting of raw materials in a following mass proportion: hydrolyzed sodium hyaluronate (1000 Daltons) 0.01%, hydrolyzed sodium hyaluronate (5000 Daltons) 0.01%, allantoin 0.01%, carbomer 0.3%, glycerol 4%, butanediol 4%, triethanolamine 0.3%, ethanol 68%, and balance water.

* * * * *